(12) United States Patent
Friedlander et al.

(10) Patent No.: US 8,495,069 B2
(45) Date of Patent: Jul. 23, 2013

(54) ASSOCIATING RECORDS IN HEALTHCARE DATABASES WITH INDIVIDUALS

(75) Inventors: Robert R. Friedlander, Southbury, CT (US); Anwer M. Khan, Irvine, CA (US)

(73) Assignee: International Business Machines Corporation, Armonk, NY (US)

( * ) Notice: Subject to any disclaimer, the term of this patent is extended or adjusted under 35 U.S.C. 154(b) by 423 days.

(21) Appl. No.: 11/850,875

(22) Filed: Sep. 6, 2007

(65) Prior Publication Data

US 2007/0299697 A1    Dec. 27, 2007

Related U.S. Application Data

(63) Continuation of application No. 10/964,418, filed on Oct. 12, 2004, now abandoned.

(51) Int. Cl.
*G06F 7/00* (2006.01)
*G06F 17/30* (2006.01)

(52) U.S. Cl.
USPC .......................................... 707/748; 707/737

(58) Field of Classification Search
CPC ............ G06F 17/3701; G06F 17/30864; G06F 17/30598; G06F 17/30705; G06F 17/30265; G06F 17/30867; G06Q 30/02; G06Q 10/10
USPC .......................... 707/748, 610, 791, 793, 796
See application file for complete search history.

(56) References Cited

U.S. PATENT DOCUMENTS

| | | | |
|---|---|---|---|
| 4,328,978 A | 5/1982 | McLaughlin | |
| 5,991,758 A | 11/1999 | Ellard | |
| 6,058,391 A | 5/2000 | Gardner | |
| 6,189,004 B1 | 2/2001 | Rassen et al. | |
| 6,385,604 B1 | 5/2002 | Bakalash et al. | |

(Continued)

FOREIGN PATENT DOCUMENTS

| | | |
|---|---|---|
| JP | 2002312373 | 4/2001 |
| JP | 2002342484 | 2/2002 |
| VU | WO 01/37097 A1 | 5/2001 |
| WO | WO 01/08077 A1 | 2/2001 |

OTHER PUBLICATIONS

Wang, C., "A COBRA-based Object Framework with Patient Identification Translation and Dynamic Linking. Methods for Exchanging Patient Data," *Methods of Information in Medicine*, vol. 38, No. 1, pp. 56-65, Mar. 1999.

(Continued)

*Primary Examiner* — Kimberly Wilson
*Assistant Examiner* — Hexing Liu
(74) *Attorney, Agent, or Firm* — Yudell Isidore Ng Russell PLLC (57) ABSTRACT

Methods for associating healthcare records in healthcare databases with an individual are provided. One or more attribute types are located in first and second records. The one or more attribute types being associated with the individual. A weighted score is determined for the located at least one attribute type based on a comparison of the located at least one attribute type in the first record and the located at least one attribute type in the second record. The weighted score indicates a likelihood that the located at least one attribute type in the first and second records are both associated with the individual. A confidence is provided and is associated with the first and second records based on the weighted score. The confidence score indicates a likelihood that both the first and second records are associated with the individual.

20 Claims, 6 Drawing Sheets

U.S. PATENT DOCUMENTS

| | | | |
|---|---|---|---|
| 6,397,224 B1* | 5/2002 | Zubeldia et al. | 707/102 |
| 6,509,898 B2 | 1/2003 | Chi et al. | |
| 6,532,459 B1* | 3/2003 | Berson | 1/1 |
| 6,578,043 B2 | 6/2003 | Nye | |
| 6,629,106 B1 | 9/2003 | Narayanaswamy et al. | |
| 6,978,268 B2 | 12/2005 | Thomas et al. | |
| 7,107,155 B2 | 9/2006 | Frudakis | |
| 2002/0059183 A1 | 5/2002 | Chen | |
| 2002/0099691 A1 | 7/2002 | Lore et al. | |
| 2002/0099692 A1 | 7/2002 | Shah et al. | |
| 2002/0156791 A1 | 10/2002 | Nesamoney et al. | |
| 2002/0184225 A1 | 12/2002 | Ghukasyan | |
| 2003/0041059 A1 | 2/2003 | Lepien | |
| 2003/0074222 A1 | 4/2003 | Rosow et al. | |
| 2003/0088438 A1 | 5/2003 | Maughan et al. | |
| 2003/0120652 A1 | 6/2003 | Tifft | |
| 2003/0126148 A1 | 7/2003 | Gropper et al. | |
| 2003/0126156 A1* | 7/2003 | Stoltenberg et al. | 707/104.1 |
| 2003/0177132 A1 | 9/2003 | Thomas et al. | |
| 2003/0191669 A1 | 10/2003 | Fitzgerald et al. | |
| 2003/0195898 A1 | 10/2003 | Agarwal et al. | |
| 2003/0233250 A1* | 12/2003 | Joffe et al. | 705/2 |
| 2004/0064449 A1 | 4/2004 | Ripley et al. | |
| 2004/0111298 A1 | 6/2004 | Schoenberg | |
| 2004/0181526 A1 | 9/2004 | Burdick et al. | |
| 2004/0220836 A1 | 11/2004 | Doherty et al. | |
| 2005/0182722 A1 | 8/2005 | Meyer et al. | |
| 2006/0041450 A1 | 2/2006 | Dugan | |

OTHER PUBLICATIONS

Gabrieli, "Guide for Unique Healthcare Identifier Model," *Journal of Clinical Computing*, vol. 21, No. 5, pp. 101-139, 1993.

Polak et al., "Using Automated Analysis of the Resting Twelve-Lead ECG to Identify Patients at Risk of Developing Transient Myocardial Ischaemia—an Application of an Adaptive Logic Network," *Physiological Measurement*, vol. 18, No. 4, pp. 317-325, Nov. 1997.

Adam et al., "Positive Patient Identification: a Practical Solution to a Challenging Problem," Toward an Electronic Patient '97. Conference and Exposition. Proceedings, Pt. vol. 3, pp. 100-108, 1997.

Chatfield, "Marketing an HMO by 'Smart' ID Cards with Patient History on an Electronic Medical Record," Proceedings. Toward an Electronic Patient Record '96. Twelfth International Symposium on the Creation of Electronic Health Record System and Global Conference on Patient Cards, Pt. vol. 1, pp. 608-620, 1996.

Sheller et al., "Smart Card Evolution," *Communications of the ACM*, vol. 45, No. 7, Jul. 2002, pp. 83-88.

Grimson et al., "The SI Challenge in Health Care," *Communications of the ACM*, vol. 43, No. 6, Jun. 2000, pp. 49-55.

Lowery et al., "Barriers to Implementing Simulation in Health Care," Proceedings from the 1994 Winter Simulation Conference, pp. 868-875.

Goodwin et al., "Data Mining for Preterm Birth Prediction," pp. 46-51.

Zarowski et al., "Some Algorithms for Circadian Rhythm Identification," 2001 IEEE Pacific Rim Conference on Communications, Computers, and Signal Processing, Pt. vol. 2, pp. 425-428, 2001.

Hoshiai et al., "SION Architecture: Semantic Information-Oriented Network Architecture," *Transactions of the Institute of Electronics, Information and Communication Engineers B.*, vol. J84-B, No. 3, pp. 411-424, Mar. 2001.

Goehring, "Identification of Patients in Medical Databases—Soundex Codes Versus Match Code," *Medical Informatics*, vol. 10, No. 1, pp. 27-34, Jan.-Mar. 1985.

Jinman Kim, A solution to the Distribution and Standardization of Multimedia Medical Data in E-Health, 2001, Australian Computer Society, Inc. Darlinghurst, Australia, Australia, ACM International Conference Proceeding Series; vol. 147 Proceedings of the Pan-Sydney area workshop on Visual information processing—vol. 11, pp. 161-164.

William Phillips, Jr. Person-matching by electronic methods, Jul. 1962, ACM Press New York, NY, USA, Communications of the ACM vol. 5, Issue 7, pp. 404-407.

Friedlander, "Systems for Associating Records in Healthcare Database with Individuals," U.S. Appl. No. 10/964,418, Non-Final Office Action dated Jan. 29, 2007.

Friedlander, "Systems for Associating Records in Healthcare Database with Individuals," U.S. Appl. No. 10/964,418, Non-Final Office Action dated Aug. 9, 2007.

Friedlander, "Systems for Associating Records in Healthcare Database with Individuals," U.S. Appl. No. 10/964,418, Final Office Action dated Jan. 23, 2008.

* cited by examiner

First Name: John
Last Name: Doe
Date: 02/02/2003
Gender: Male
SS#: 133-99-7754
Height: 6'2"
Weight: 195
DOB: 01/14/1974
Blood Type: A+
Patient_ID#: P40406070
Database Links:
   HMO Database(PR 230a)
   Hospital Database (PR 235a)

Patient Record 310a

First Name: John
Last Name: Doe
Date: 01/05/2000
Gender: Male
SS#: 133-99-7754
Height: 6'1"
Weight: 165
Blood Type: A+
Address:
   111 Main Street
   Houston, TX 22557
Phone No: 870-4455

Patient Record 230a

First Name: John
Last Name: Doe
Date: 05/02/2002
Gender: Male
Height: 6'2"
Weight: 187
DOB: 01/14/1974
Address:
   222 West Huron St.
   Houston, TX 55667

Patient Record 235a

First Name: John
Last Name: Doe
Date: 02/05/2003
Gender: Male
SS#: 666-72-9903
Height: 5'4"
Weight: 145
DOB: 06/07/1964
Blood Type: O-

Patient Record 235d

ASSOCIATING RECORDS IN HEALTHCARE DATABASES WITH INDIVIDUALS

RELATED APPLICATION

The present application claims the benefit of priority as a continuation of U.S. application Ser. No. 10/964,418, filed Oct. 12, 2004 now abandoned, which is entitled "SYSTEMS FOR ASSOCIATING RECORDS IN HEALTHCARE DATABASES WITH INDIVIDUALS", the disclosure of which is hereby incorporated herein by reference as if set forth in its entirety.

FIELD OF THE INVENTION

The invention relates to database management in general and, more particularly, to organization and verification of data stored in databases.

BACKGROUND OF THE INVENTION

As the field of healthcare continues to become more specialized, the provision of services by many healthcare workers and/or providers to many patients may increase. In order to accomplish this, healthcare delivery has been organized into specialized departments or healthcare sources such as, for example, nursing, laboratory, pharmacy, and radiology departments. Each department has the responsibility for accomplishing its particular, often specialized, subset of tasks. Sometimes the departments are associated with different healthcare enterprises or offices having different geographic locations. Unfortunately, this has resulted in suboptimal healthcare operations because patient information related to a single patient that is stored at various departments may not be easily accessible from a single place.

Conventional healthcare information systems (HIS) combine patient related information for a particular patient from multiple, different healthcare sources into a single consolidated database, having a master patient index (MPI), using various record matching techniques. However, these systems may experience many problems and may not provide very accurate results. For example, the conventional record matching techniques may incorrectly combine two patient's information if two patients have the same name. Furthermore, conventional record matching techniques may combine multiple copies of the same patient information creating a duplicate record or may not locate critical patient information that is related to the same patient, which may result in an improper diagnosis. Current matching techniques may generate an unacceptable number of false matches, duplicate matches and/or miss matches. Conventional methods for storing and/or or accessing medical data in and/or from databases that attempt to address the problems discussed above, are discussed in, for example, United States Patent Publication Nos. US 2003/0088438 and US 2003/0177132. However, there is a need for improved record matching techniques to allow generation of a combined patient record that can be relied upon for the provision of healthcare to the patient.

SUMMARY OF THE INVENTION

Some embodiments of the present invention provide methods for associating healthcare records in healthcare databases with an individual. One or more attribute types are located in first and second records. The one or more attribute types are associated with the individual. A weighted score is determined for the located at least one attribute type based on a comparison of the located at least one attribute type in the first and second records are both associated with the individual. A confidence score associated with the first and second records is provided based on the weighted score. The confidence score indicates a likelihood that both the first and second records are associated with the individual.

In further embodiments of the present invention, logic may be applied to the weighted score to provide the confidence score. The first and second records may be located in first and second databases, respectively. The first and second databases may be the same database.

In still farther embodiments of the present invention, one or more attribute types associated with the individual may be obtained from the first record in a first database on a local server. The obtained one or more attribute types may be located in the second record in a second database on a remote server. The attribute types may include a first name, last name, a social security number, a gender, a birth date, an address, a telephone number, a birth place, a blood type, an age, a height, a weight and/or a gene signature.

In some embodiments of the present invention, the individual may be assigned an identifier so as to allow future identification of the individual. The identifier may be associated with the first and second records if the confidence score meets a predetermined threshold. In certain embodiments of the present invention, the information in the first and second records may be combined into a third complete record if the confidence score meets a predetermined threshold.

In further embodiments of the present invention, a first attribute type associated with the individual may be located in the first and second records and a second attribute type may be located in the first and second records. A first weighted score may be determined based on a comparison of the located first attribute type in the first record and the located first attribute type in the second record and a second weighted score may be determined based on a comparison of the located second attribute type in the first record and the located second attribute type in the second record. The confidence score may be provided by applying logic to the first and second weighted scores.

DETAILED DESCRIPTION OF EMBODIMENTS OF THE INVENTION

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will be appreciated by one of skill in the art, the invention may be embodied as a method, data processing system, or computer program product. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language or in a visually oriented programming environment, such as Visual/Basic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to a flowchart illustration and/or block diagrams of methods, systems, computer program products and data structures according to embodiments of the invention. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Embodiments of the present invention will now be discussed with respect to FIGS. 1 through 6. As described herein, records located in one or more healthcare databases may be accurately associated with an individual. In particular, one or more attribute types, for example, gender, height, weight, blood type and the like, associated with the individual may be obtained. The attribute types may be obtained by, for example, entering the name of the individual into a first database and obtaining a first record in the first database having the name of the individual. The individual's name and/or the attribute types contained in the first record may be located in one or more additional records in the first database or in one or more remote databases. Similar attribute types in the located records may be compared. For example, if five records exist having the individual's name in the "name" field, the social security number attribute types in these records may be located and compared. A weighted score indicating the likelihood that the located attribute types (social security number) in the multiple records are associated with the same individual may be determined. For example, if the social security numbers in two records match, the weighted score may indicate that there is a 100 percent likelihood that both of the attribute types belong to the same individual. If, on the other hand, the social security numbers do not match, the weighted score may indicate that there is a 0 percent likelihood that both attribute types belong to the same individual. Using the weighted scores identified for each of the attribute types in the located records, a confidence score may be generated for each of the located records indicating the likelihood that the records belong to the same individual. For example, the confidence score for a particular record may indicate that there is a 92 percent likelihood that a record belongs to the individual. Thus, the confidence score may provide an indication of the accuracy of the matching process, which may be used to decide whether or not to provide medical services to the individual as discussed further herein below.

Figure 1:
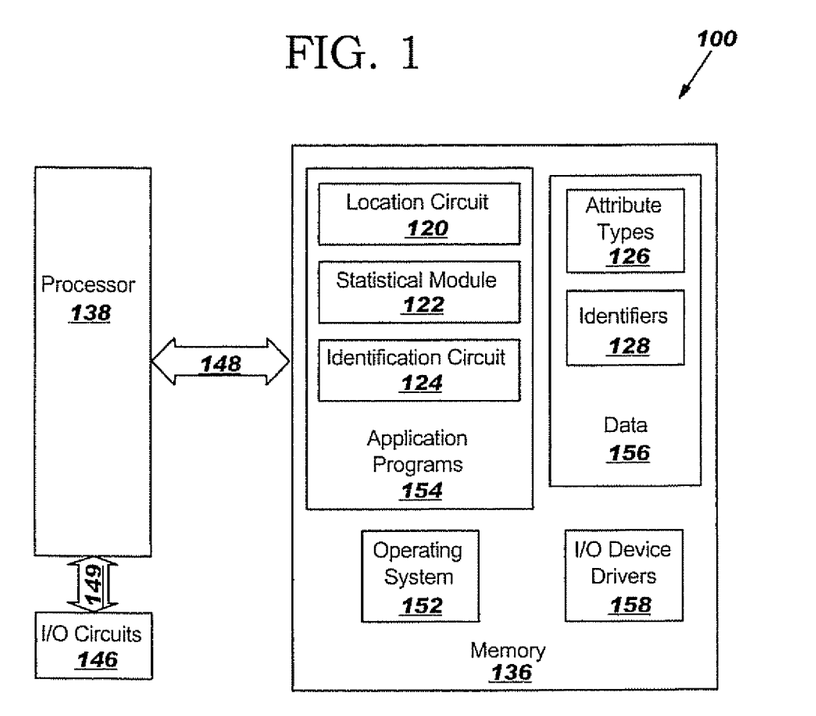
FIG. 1 is a block diagram illustrating data processing systems according to some embodiments of the present invention.

FIG. 1 illustrates an exemplary data processing system 100 or database environment that may be included in devices operating in accordance with some embodiments of the present invention. As illustrated, the data processing system 100 includes a processor 138, a memory 136 and input/output circuits 146. The data processing system 100 may be incorporated in, for example, a personal computer, server, router or the like. The processor 138 communicates with the memory 136 via an address/data bus 148 and communicates with the input/output circuits 146 via an address/data bus 149. The input/output circuits 146 can be used to transfer information between the memory 136 and another computer system or a network using, for example, an Internet protocol (IP) connection. These components may be conventional components such as those used in many conventional data processing systems, which may be configured to operate as described herein.

In particular, the processor 138 can be any commercially available or custom microprocessor, microcontroller, digital signal processor or the like. The memory 136 may include any memory devices containing the software and data used to implement the functionality circuits or modules used in accordance with embodiments of the present invention. The memory 136 can include, but is not limited to, the following types of devices: cache, ROM, PROM, EPROM, EEPROM, flash memory, SRAM, DRAM and magnetic disk. In some embodiments of the present invention, the memory 136 may be a content addressable memory (CAM).

As further illustrated in FIG. 1, the memory 136 may include several categories of software and data used in the data processing system 100: an operating system 152; application programs 154; input/output device drivers 158; and data 156. As will be appreciated by those of skill in the art, the operating system 152 may be any operating system suitable for use with a data processing system, such as OS/2, AIX or zOS from International Business Machines Corporation, Armonk, N.Y., Windows95, Windows98, Windows2000 or WindowsXP from Microsoft Corporation, Redmond, Wash., Unix or Linux. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154, the operating system 152, the input/output device drivers 158, and other software programs that may reside in the memory 136. As illustrated in FIG. 1, the data 156 may include attribute type data 126 and patient identifier data 128 for use by the circuits and modules of the application programs 154 according to some embodiments of the present invention as discussed further herein.

As further illustrated in FIG. 1, according to some embodiments of the present invention the application programs 154 include a location circuit 120, a statistical module 122 and an identification circuit 124. The location circuit 120 may be configured to receive an input, such as, a name of an individual and/or an attribute type 126 associated therewith. The attribute types may be located in a record having the individual's name. The record may be located in a local database or a remote database. The individual may be a patient, physician or healthcare provider without departing from the scope of the present invention. As used herein, an "attribute type" refers to any category of information that may be associated with an individual that can be used for identification purposes. For example, attribute types according to some embodiments of the present invention may include, for example, first name, last name, social security number, gender, birth date, address, telephone number, birth place, blood type, age, height, weight, eye color, hair color, race and/or gene signature, such as a single nucleotide polymorphism (SNP). It will be understood that this list of attribute types is provided for exemplary purposes only and that embodiments of the present are not limited to the attribute types set out herein.

The location circuit 120 may be further configured to locate one or more records including the patient's name and/or attribute types associated therewith in multiple databases. For example, if the patient is a member of an HMO, the database for the HMO may include patient information associated with the patient. Furthermore, a hospital in which the patient has been treated may also have a database, which may include information about the patient. More than one record located using the patient's name and/or attributes associated therewith may be located in each of the databases.

The statistical module 122 may be configured to compare the attribute types located in the multiple records. For example, two patient records, one located in the HMO database and one located in the hospital database, may include an attribute type directed to blood type, the blood types in the two patient records may be compared to determine if they are the same. The statistical module 122 may be further configured to calculate a weighted score for the located attribute type based on the result of the comparison of the located at attribute types in the record of the HMO database and the record of the hospital database. The weighted score may indicate the likelihood that the attribute types located in the record of the HMO database and the record of the hospital database are both associated with the same individual. For example, if the blood types match, the weighted score may indicate a 100 percent likelihood that the attribute types both belong to the same individual. On the other hand, if the blood types do not match, the weighted score may indicate a 0 percent likelihood that the attribute types belong to the same individual. A weighted score may be calculated for each of the similar attribute types in the located records.

It will be understood that "comparing" or "comparison", as used herein, refers not only to a simple comparison, i.e., the attribute types match or do not match, but also to a more complicated comparison that may assess the likelihood that two attribute types are similar enough to belong to the same patient or may have changed over the period of time between records. For example, hazel eyes may sometimes appear green and other times appear brown. Thus, an individual associated with a record indicating a hazel eye color may be the same individual associated with a record indicating a green eye color. Furthermore, it is common for people to change their hair color. Thus, an individual associated with a record indicating a brown hair color may be the same individual associated with a record indicating a red hair color. The fact that some attribute types may change over time or are subject to multiple interpretations may be taken into account in the calculation of the weighted score for the attribute type. Furthermore, attribute types that may change over time or are subject to different interpretations may be given less weight in the calculation of an overall confidence score than those attribute types that are fixed as discussed further below.

It will be further understood that devices and systems according to some embodiments of the present invention are capable of learning from the previous record comparisons. For example, if it is determined that two records belong to the same individual even though one of the records indicated eye color as brown and one of the records indicated eye color as hazel, devices and systems according to embodiments of the present invention may use this information and adjust the weighting given to these attribute types the next time this scenario occurs. Furthermore, devices and systems according to embodiments of the present invention may be also learn which computational logic and statistical algorithms obtain the best results and use these more frequently.

Although embodiments of the present invention are discussed above with respect to two databases, more than two databases may be searched without departing from the scope of the present invention. Furthermore, more than one record may be located in each database. For example, if a patient comes into the emergency room twice and on the first visit the healthcare provider enters her name spelled correctly and on the second visit the healthcare provider enters her name spelled incorrectly, this patient will have two records in the hospital's database. According to some embodiments of the present invention, the second record having the misspelled name may be located using other attribute types associated with the patient.

The identification circuit 124 may be configured to provide a confidence score based on the weighted score associated with each of the attribute types located in multiple records. For example, if three patient records having the name of the individual are located in three different databases, the statistical module 122 may be configured to calculate a weighted score for each of the attribute types that at least two of the records have in common. The identification circuit 124 may be further configured to use the generated weighted scores as an input and calculate an overall confidence score that indicates the likelihood that the located records belong to the same individual. If the confidence score indicates that there is a 99.9 percent likelihood that a record belongs to the individual, a healthcare provider may be able to rely on the information in these records in the provision of healthcare services to this individual. If, on the other hand, the confidence score indicates that there is only a 50 percent likelihood that the record belongs to the individual, this record may not be a reliable source for the provision of healthcare services. For example, if the record having a confidence score indicating a 50 percent likelihood that the record belongs to the individual indicates the individual's blood type, the healthcare provider may not wish to rely on this information, as provision of blood of the wrong type to a patient could cause serious damage. It will be understood that in some embodiments of the present invention, the confidence score is provided for illustrative purposes and may be spread for ease of understanding.

In some embodiments of the present invention, the identification circuit 124 may be configured to assign an identifier 128, which may be associated with the records located in each of the databases having a specified confidence score and/or the individual himself. The identifier 128 may be stored in, for example, a database on a device in a doctor's office, and may allow future identification of the individual and the records associated therewith. In certain embodiments of the present invention, the records located having a specified confidence score may be combined into a single record on a specific database, for example, the database at the doctor's office, or software links may be created between the local database at the doctor's office and the remote databases in which the records having a specified confidence score were located. Weighted scores may also be updated through the links as data from records stored at the remote databases are added to or combined with records stored at the local database.

In some embodiments of the present invention, the identification circuit 124 may apply computational logic and/or use statistical algorithms to generate the confidence score associated with the records. The computational logic and statistical algorithms that may be used are known to those having skill in the art and, therefore, will not be discussed further herein.

While the present invention is illustrated with reference to the location circuit 120, the statistical module 122 and the identification circuit 124 being application programs in FIG. 1, as will be appreciated by those of skill in the art, other configurations fall within the scope of the present invention. For example, rather than being application programs 154, these circuits and modules may also be incorporated into the operating system 152 or other such logical division of the data processing system 100. Furthermore, while the location circuit 120, the statistical module 122 and the identification circuit 124 are illustrated in a single data processing system, as will be appreciated by those of skill in the art, such functionality may be distributed across one or more data processing systems. Thus, the present invention should not be construed as limited to the configuration illustrated in FIG. 1, but may be provided by other arrangements and/or divisions of functions between data processing systems. For example, although FIG. 1 is illustrated as having various circuits and modules, one or more of these circuits or modules may be combined without departing from the scope of the present invention.

Figure 2:
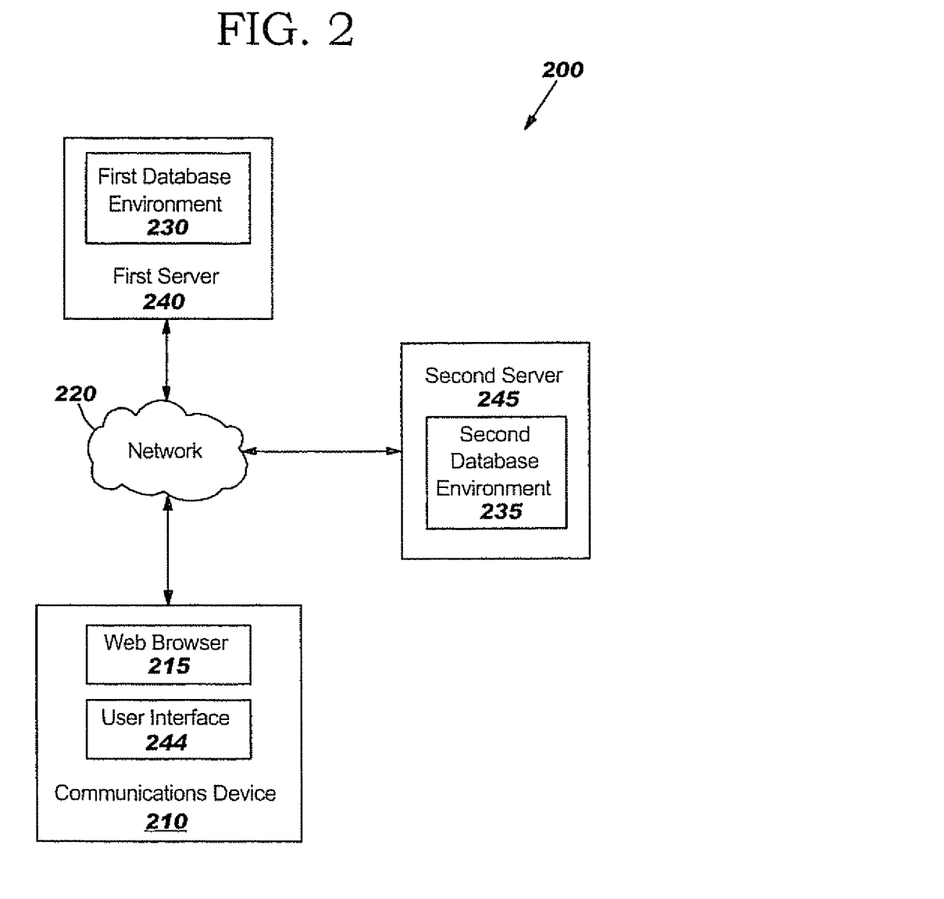
FIG. 2 is a block diagram illustrating an exemplary network environment for operations and devices according to some embodiments of the present invention.

FIG. 2 illustrates an exemplary environment 200 for operations and devices according to some embodiments of the present invention. As illustrated in FIG. 2, the environment 200 may include a communications device 210, a network 220, a first server 240 and a second server 245. It will be understood that the communications device 210 illustrated in FIG. 2 may include the data processing system 100 or database environment discussed above with respect to FIG. 1. The communications device 210 may be, for example, a laptop computer, a desktop computer, a personal data assistant (PDA), a web capable mobile terminal or any device capable of communicating with the network 220. The communications device 210 may include a user interface 244, which may be used to enter a name of an individual and/or one or more attribute types associated therewith, and a web browser 215 that may be accessed through the user interface 244. The first and second servers 240 and 245 may include first and second database environments 230 and 235, respectively, which may include patient records for use in some embodiments of the present invention. The communications device 210 may communicate over the network 220, for example, the internet, through a telephone line, a digital subscriber link (DSL), a broadband cable link, a wireless link or the like. The first and second servers 240 and 245 may also communicate over the network 220. Thus, the network 220 may convey data between the communications device 210 and the first and second servers 240 and 245.

Exemplary operations of methods and devices according to some embodiments of the present invention will now be discussed with respect to FIG. 2. A patient may have an appointment at a doctor's office and may provide his name, John Doe, to the person doing intake at the doctor's office. The doctor's office may include a communications device 210 including a data processing system 100 or database environment according to embodiments of the present invention. The person doing intake at the doctor's office may enter the patient's name, John Doe, using the user interface 244 of the communications device 210. For example, the user interface 244 may be a graphical interface that requests such information as patient's name, address, phone number, social security number, blood type, and any other relevant attribute type. Alternatively, the patient's name may be used to provide access to a patient record or records stored in a database associated with the doctor's office. Devices and methods according to embodiments of the present invention may be configured to located records having names similar to the patients name. For example, in this example, embodiments of the present invention may be configured to locate records having the following names associated therewith: Jonathon Doe, Jon Doe, John S. Doe, John Steven Doe and the like. This database may be stored at the communications device 210 or at a remote server associated with the communications device without departing from the scope of the present invention.

The web browser 215 may be used to access other healthcare databases to obtain more information about the patient and the patient's medical history. Using the web browser 215, the patient's name and the attribute types associated therewith may be used to access a first database environment 230 at a first server 240 and a second database environment 235 at a second server 245. The first and second database environments 230 and 235 may include patient records. The first database environment 230 may be associated with an HMO and the second database environment 235 may be associated with a hospital. The web browser 215 may communicate the patient's name and/or the attribute types associated therewith over the network 220 to the first and second servers 240 and 245. As discussed above, the patient's name and associated attribute types may be used to locate one or more patient records stored in the first and second database environments 230 and 235.

Figure 3:
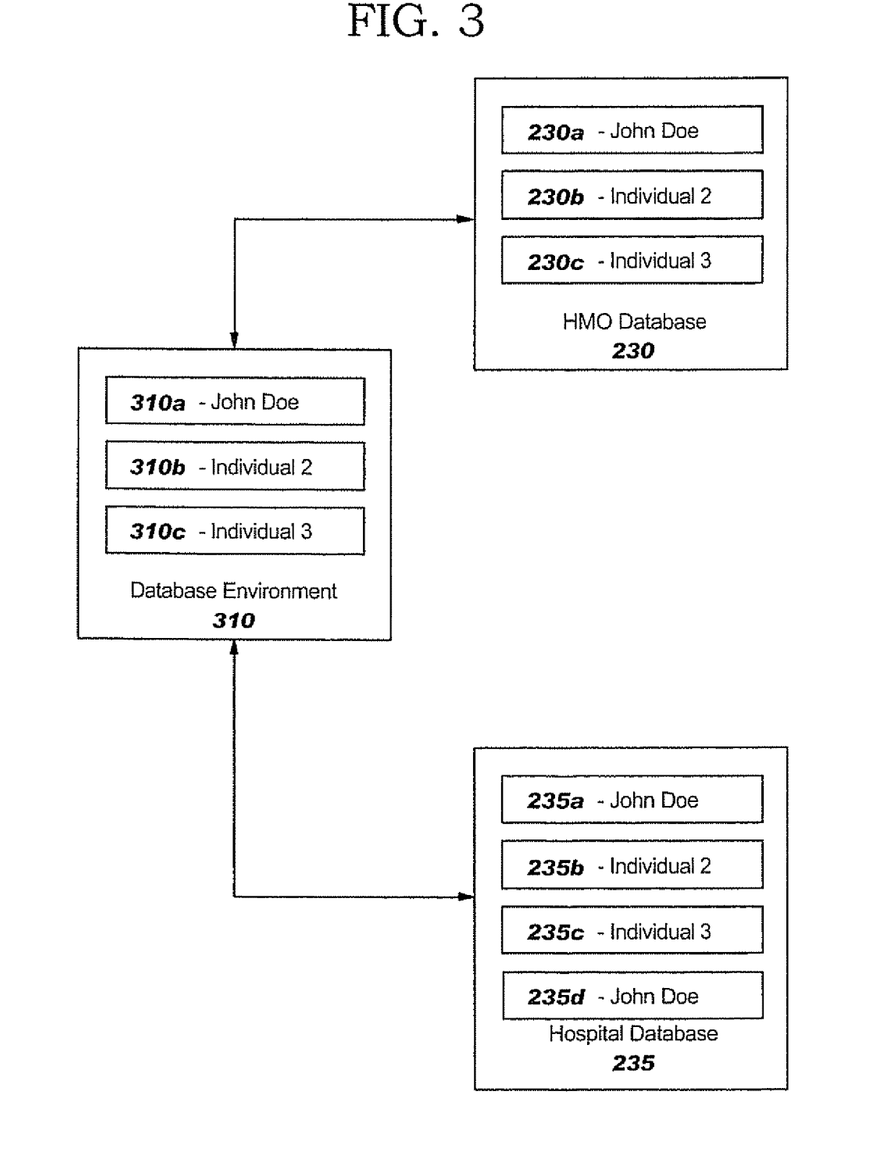
FIG. 3 is a schematic illustration of relationships between a database environment according to some embodiments of the present invention and existing HMO and/or hospital databases.

Exemplary database environments and patient records according to some embodiments of the present invention are illustrated in FIGS. 3 and 4, respectively. The example of John Doe will be discussed further with respect to FIGS. 2, 3 and 4. As illustrated in FIG. 3, a database environment 310 is provided at the doctor's office and has access to the HMO database 230 and the Hospital database 235 via the network 220. As further illustrated, each of the database environments 310, 230 and 235 include multiple patient records. In particular, database 310 includes three patient records 310a, 310b and 310c, the HMO database 230 includes three patient records 230a, 230b and 230c and the Hospital database 235 includes four patient records 235a, 235b, 235c and 235d. As illustrated, each of the databases has at least one patient record directed to a "John Doe," i.e., patient records 310a, 230a, 235a and 235d. The details of the four patient records 310a, 230a, 235a and 235d are illustrated out in FIGS. 4A through 4D.

As illustrated in FIGS. 4A through 4D, each of the patient records 310a, 230a, 235a and 235d include data associated with one or more of the following attribute types: first name, last name, date of visit, gender, social security number, height, weight, date of birth (DOB), blood type, address and telephone number. As further illustrated, all of the records 310a, 230a, 235a and 235d do not necessarily include the same attribute types. Furthermore, patient record 310a, which belongs to the patient, John Doe in this example, also includes a patient identifier, that may be associated with John Doe and used to access records associated with John Doe in accordance with some embodiments of the present invention as discussed further below. According to some embodiments of the present invention, once these records 310a, 230a, 235a and 235d are located, the similar attribute types in each of the located records 310a, 230a, 235a and 235d are compared. In particular, the attribute type associated with gender is provided in all four patient records 310a, 230a, 235a and 235d, and all four records 310a, 230a, 235a and 235d indicate that John Doe is male. Thus, the gender attribute type for each of the patient records 310a, 230a, 235a and 235d is given a weighted score indicating a 100 percent likelihood that all four records 310a, 230a, 235a and 235d belong to John Doe. However, because gender can only be either male or female, the gender attribute type may not be the most informative attribute type. Thus, the weighted score for gender may not be given as much consideration as other more informative attribute types in the calculation of the overall confidence score for the record as discussed further below.

The attribute type associated with Social Security No. (SS#) is provided in three records 310a, 230a and 235d out of the four records 310a, 230a, 235a and 235d. The SS# attribute types match in two of the patient records 310a and 230a of the database 310 and the HMO database 230, respectively, but do not match the SS# attribute type in the patient record 235d of the hospital database 235. Thus, the weighted score for the SS# attribute type assigned to the patient records 310a and 230a of the database 310 and the HMO database 230, may indicate a 100 percent likelihood that both of these records 310a and 230a belong to John Doe. However, the weighted score given to the SS# attribute type assigned to the patient record 235d of the hospital database 235 may indicate a 0 percent likelihood that this record 235a belongs to John Doe.

The reliability of the attribute type directed to social security number may depend on the facility in which the social security number is supplied. For example, in a public hospital in a large city, such as Atlanta, a social security number may not provide useful information due to a large number of illegal immigrants using the same social security number. In other words, multiple patients may be in the database having the same social security number, therefore, reducing the reliability of a match of this attribute type. However, in an exclusive private clinic, the use of the social security number for identification purposes may be so accurate as to be the only piece of information needed for identification. Thus, the weighting given to a particular weighted score when calculating the confidence score for the record may vary from institution to institution. Similarly, the weighting given to information found in the records may also be based on the system the information is provided from. In other words, some databases are more reliable than others. For example, if the information is provided from a "gold standard database," the information provided from this database may be given a higher weight than other records to which it is being compared.

As further illustrated in FIGS. 4A through 4D, each of the four records 310a, 230a, 235a and 235d includes an attribute type directed to height. The height attribute type matches in two patient records 310a and 235a out of the four patient records 310a, 230a, 235a and 235d provided. Furthermore, the height attribute type provided in patient record 230a is only off by an inch, but the height attribute type provided in the patient record 235d is off by almost a foot. Accordingly, it is likely that the weighted score for the height attribute type assigned to the patient records 310a and 235a may indicate a 100 percent likelihood that both of these records belong to John Doe and the height attribute type assigned to the patient records 230a may indicate almost a 100 percent likelihood that this record belongs to John Doe as a small variation in height measurement may be expected. However, the weighted score given to the height attribute type of patient record 235d may be very low as a height variation of almost a foot would not be expected.

Each of the four records 310a, 230a, 235a and 235d also include an attribute type directed to weight. The weight attribute type does not match in any of the four patient records 310a, 230a, 235a and 235d provided. However, this may be expected as John Doe visited these facilities on different days and a slight weight fluctuation may be normal. In particular, the difference in weight between the patient record 310a and the patient record 230a is 30 pounds, which may indicate a non-match of records. However, the weights were measured over 3 years apart. It is feasible that someone could gain 30 pounds in three years. The time delta between the weight measurements may betaken into account when calculating the weighted score for these records. The difference in weight between the patient record 310a and the patient record 235a is only 7 pounds and the weights were measured over a year apart. Again, the time delta between the weight measurements may betaken into account when calculating the weighted score for these records. Finally, the difference in weight between the patient record 310a and the patient record 235d is 50 pounds and these weights were only measured three days apart, which may indicate a non-match of these records. In some embodiments of the present invention, a user of the communications device 210 may be prompted to answer a question with respect to the result of the comparison. In this example, the user of the communications device 210 may be prompted to decide the relevance of the difference in weights.

The attribute type associated with date of birth (DOB) is provided in three 310a, 235a and 235d out of the four records 310a, 230a, 235a and 235d. The DOB attribute type match in the patient records 310a and 235a of the database 310 and the hospital database 235, but do not match the DOB attribute in the patient record 235d of the hospital database 235. Thus, the weighted score for the DOB attribute type assigned to the patient records 310a and 235a of the database 310 and the hospital database 235, may indicate a 100 percent likelihood that both of these records belong to John Doe. However, the weighted score given to the DOB attribute type assigned to the patient record 235d of the hospital database 235 may indicate a 0 percent likelihood that this record belongs to John Doe.

The attribute type associated with blood type is provided in three records 310a, 230a and 235d out of the four records 310a, 230a, 235a and 235d. The blood type attribute types match in the patient records 310a and 230a of the database 310 and the HMO database 230, but do not match the blood type attribute in the patient record 235d of the hospital database 235. Thus, the weighted score for the blood type attribute type assigned to the patient records 310a and 230a, may indicate a 100 percent likelihood that both of these attributes belong to John Doe. However, the weighted score given to the blood type attribute type assigned to the patient record 235d may indicate a 0 percent likelihood that this attribute belongs to John Doe.

Finally, the attribute type associated with address is provided in two records 230a and 235a out of the four records 310a, 230a, 235a and 235d. The addresses in the two records 230a and 235a do not match. However, this may be expected as John Doe visited these facilities on different days two years apart and it is possible that he may have moved. Both addresses are in Houston Texas, which may be further evidence that these two records are both associated with John Doe. The time delta between the addresses and the fact that both addresses are in Houston may be taken into account when calculating the weighted score for these attribute types.

Once the weighted scores are calculated for all of the attribute types located in two or more databases as discussed above, a confidence score associated with the patient records 230a, 235a and 235d may be calculated. As discussed above, in some embodiments of the present invention, the weighted scores may be calculated using computational logic and statistical algorithms known to those having skill in the art and, thus, will not be discussed further herein.

As discussed briefly above, when calculating the likelihood that two patient records belong to a same patient, for example, John Doe in this example, some attribute types may be given more weight in the calculation of the confidence score as discussed above. The amount of weight given may vary from institution to institution as well as based on the type of information the attribute type provides. For example, gender may be given less weight than blood type, which may be given less weight than gene signatures.

Figure 4A:
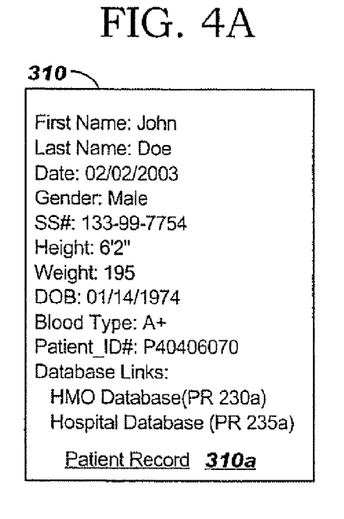
FIGS. 4A through 4D illustrate exemplary patient records and the type of data included therein according to some embodiments of the present invention.
Figure 4B:
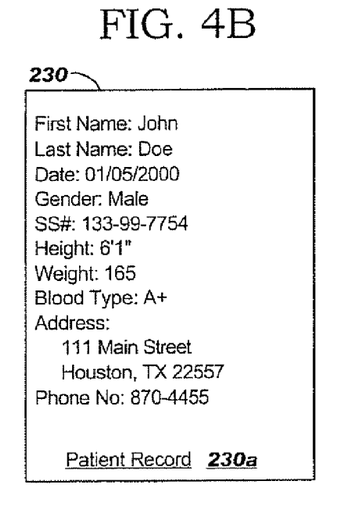
Figure 4C:
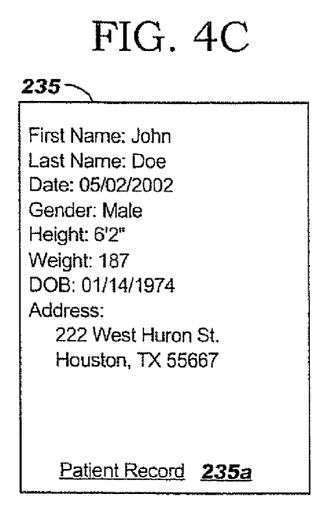
Figure 4D:
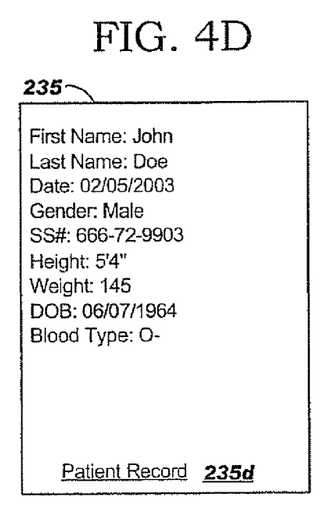

With respect to the specific example discussed above, it appears that patient record 235d will not be presented as being associated with John Doe with a very high confidence score. For example, there may be a 5 percent or less likelihood that the John Doe associated with the patient record 235d is the same John Doe associated with the patient record 310a. On the other hand, the confidence score associated with patient records 230a and 235a may be very high and it is likely that these records belong to the same John Doe associated with patient record 310a. In other words, the confidence score associated with patient records 230a and 235a may be 95 percent or higher.

It will be understood that the facility using devices and methods according to embodiments of the present invention may customize the confidence score to be met before a particular action is to take place. For example, if a patient will be a recipient of a medical procedure, the confidence score that should be met may berelatively high, for example, 95 percent or above. However, if the patient information is being used to forward a bill for medical services rendered, the confidence score to be met may be much lower, for example, 70 percent or higher.

In some embodiments of the present invention, when a high enough confidence score is met (threshold), for example, 95 percent or higher, the information in the records having these confidence scores, patient records 230a and 235a in this example, may be incorporated in the record 310a of the database environment 310. Alternatively, the database environment 310 may be configured to have links so as to allow access to patient records 230a and 235a as illustrated in patient record 310a. Furthermore, the patient identification number associated with patient record 310a may be associated with patient records 230a and 235a so as to allow future access to these records very quickly by providing the patient identification number. The identification number may be associated with a whole patient record or each piece of information (attribute-type) contained in the record without departing from the scope of the present invention.

It will be further understood that although exemplary embodiments of the present invention are discussed herein with respect to identification and verification of patient records, embodiments of the present invention are not limited to this configuration. For example, techniques used by devices and methods of the present invention may be used to identify physicians and/or other healthcare professionals without departing from the scope of the present invention. Thus, some embodiments of the present invention may be used to match patients with their physicians. For example, if the output of the database indicates that the physician performing a trauma surgery at 2AM on a particular patient is also the dean of the Medical school, the confidence score associated with this physician/patient match may be very low.

Figure 5:
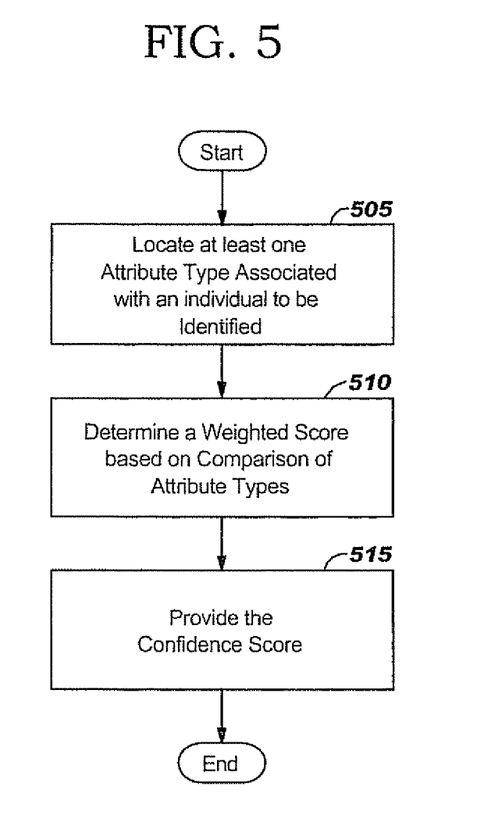
FIG. 5 is flowchart illustrating operations according to some embodiments of the present invention.

Operations according to some embodiments of the present invention will now be discussed with respect to FIGS. 5 and 6. Referring now to FIG. 5, operations begin at block 505 by locating at least one attribute type associated with an individual, for example, a patient or physician, in first and second records. The at least one attribute may be, for example, a social security number, a gender, a birth date, an address, a telephone number, a birth place, a blood type, an age, a height, a weight and/or a gene signature. The first and second records may be located in first and second databases, respectively, associated with an HMO and a hospital, respectively. A weighted score for the located at least one attribute type is determined based on a comparison of the located at least one attribute type in the first record and the located at least one attribute type in the second record (block 510). The weighted score may indicate the likelihood that the located at least one attribute type in the first and second records are associated with the individual. A confidence score may be provided that is associated with the first and second records based on the weighted scores (block 515). The confidence score may indicate a likelihood that both the first and second records are associated with the individual.

Figure 6:
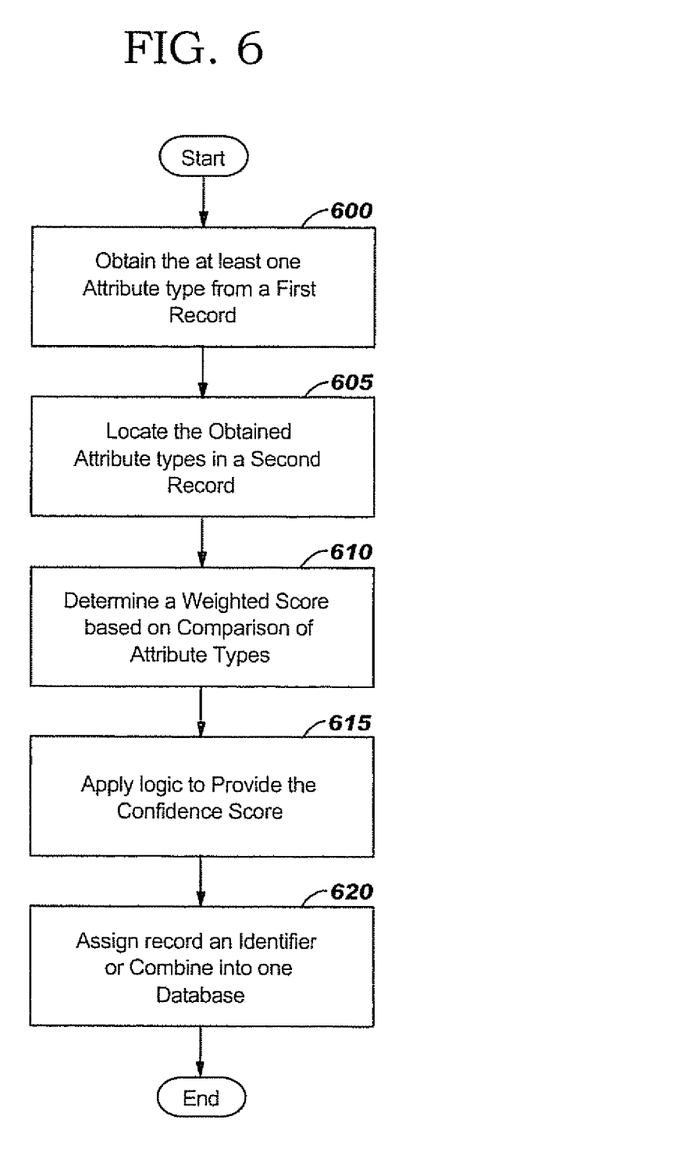
FIG. 6 is flowchart illustrating operations according to further embodiments of the present invention.

Referring now to FIG. 6, operations begin at block 600 by obtaining at least one attribute type associated with the individual from a first record in a first database on a local server. For example, a patient, John Doe, may enter a hospital using a database according to some embodiments of the present invention, and his name "John Doe" is entered into the database. Attribute types associated with John Doe may be provided from a record on a hospital database. The attribute types provided may be located in a second record in a second database, for example, a database associated with an HMO or a hospital(block 605). A weighted score for each of the located attribute types is determined based on a comparison of the located attribute types in the first and second records (block 610). The weighted score may indicate the likelihood that the located at least one attribute type in the first and second records are associated with the individual. A confidence score may be provided that is associated with the first and second records based on the weighted scores (block 615). The confidence score may indicate a likelihood that both the first and second records are associated with the individual. Once it has been determined that the record including the located attribute types belongs to the individual, an identification number may be associated with the records and/or the attribute types themselves or the information in the record may be combined with the information from the first record to create a single unified record associated with John Doe (block 620). This identification number may be used to access patient records associated with John Doe more easily in the future.

As briefly discussed above with respect to FIGS. 1 through 6, some embodiments of the present invention provide devices and methods for verifying that patient records stored in multiple databases are associated with a same patient or individual. Computational logic and statistical algorithms may be used to provide, to a specified confidence score, a likelihood that the records in the databases belong to a same individual. Thus, embodiments of the present invention may allow the number of false positive and/or negative identifications of patients to be reduced.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

That which is claimed is:

1. A method of associating healthcare records in healthcare databases with an individual, comprising:
    locating at least one attribute type in a first record of a first database and one or more similar attribute types in one or more other records of one or more other databases different from the first database, the at least one attribute type being associated with the individual;
    comparing the at least one attribute type and each of the one or more similar attribute types;
    in response to comparing the at least one attribute type and each of the one or more similar attribute types, determining, based on the comparison, a first weighted score for each one of the at least one attribute type in the first record and another weighted score for each one of the one or more similar attribute types in the one or more other records, wherein a weighted score for a particular attribute type indicates a likelihood that the particular attribute type is associated with a same individual as at least one other attribute type located in another record, and wherein a weighted score for a particular attribute type further accounts for a time delta between measurements of the particular attribute type in a particular record and measurements of one or more similar attribute types in one or more other records; and
    calculating a first confidence score output for the first record and one or more other confidence score outputs for each of the one or more other records, wherein a confidence score output of a record is based on all weighted scores of that record and indicates a likelihood that record is associated with the same individual.

2. The method of claim 1, wherein the calculating the confidence score output further comprises: applying logic to the weighted score.

3. The method of claim 1, wherein the first and second databases are the same database.

4. The method of claim 1, wherein the locating the at least one attribute type further comprises:
    obtaining the at least one attribute type from the first record in the first database on a local server; and
    locating the one or more similar one attribute types in the one or more second records in one or more second databases on a remote server;
    wherein the at least one attribute type comprises a first name, last name, a social security number, a gender, a birth date, an address, a telephone number, a birth place, a blood type, an age, a height, a weight, eye color, hair color, race and/or a gene signature.

5. The method of claim 1, further comprising:
    assigning the individual an identifier so as to allow future identification of the individual; and
    in response to a confidence score of one or more of the first record and the one or more other records meeting a predetermined threshold, associating the identifier with the of one or more of first record and the one or more other records.

6. The method of claim 5, further comprising:
    in response to the confidence score of one or more of the first record and the one or more other records meeting the predetermined threshold: combining information in the first record and the one or more other records into a third complete record.

7. The method of claim 1, wherein:
the locating at least one attribute type comprises locating a first attribute type associated with the individual in the first record and in the one or more other records and locating a second attribute type associated with the individual in the first record and in the one or more other records;
the determining a weighted score comprises:
determining a first weighted score based on a comparison of the located first attribute type in the first record and the located one or more similar attribute types in the one or more other records; and
determining the one or more other weighted scores based on a comparison of the located first attribute type in the first record and the located one or more similar attribute types in the one or more other records; and
the calculating the confidence score output comprises applying logic to the first weighted score and the one or more other weighted scores to provide the confidence score output associated with the first record and the confidence score outputs for each of the one or more other records based on the first score and the one or more other weighted scores.

8. The method of claim 1, carried out by processor execution of software code from a computer program product embodied in a computer readable storage medium.

9. The method of claim 1, further comprising:
detecting presence of an easily changed attribute type in the at least one attribute type in the first record and the one or more similar attribute types in the one or more other records, wherein the easily changed attribute type is an attribute that may change over time or is subject to more than one interpretation; and
assessing a likelihood that one or more easily changed attributes are similar enough to belong to a same individual;
wherein the one or more easily changed attributes are at least one of specific attribute types that may change over time and specific attribute types that are subject to multiple interpretations; and
wherein the confidence score output factors the easily changed attribute type in the at least one attribute type in the first record and the one or more similar attribute types in the one or more other records, wherein the easily changed attribute type is given less weight than a fixed attribute type in calculating an overall confidence score output.

10. The method of claim 1, further comprising:
analyzing a comparison data of one or more previous comparisons;
adjusting the first weighted score for the located at least one attribute type based on the comparison data; and
in response to a comparison indicating a match, recording new comparison data based on the matched attributes, wherein the comparison data also identifies attributes types, computational logic, and statistical algorithms for obtaining the best matching results.

11. The method of claim 9, further comprising learning from a previous comparison that a selected attribute type is the easily changed attribute type by determining that two records are for a selected individual and that the two records have different data for the selected attribute type.

12. The method of claim 1, further comprising:
during the calculating of a confidence score output, increasing or reducing a weight given to one or more attribute types based on an institution the one or more attribute types belongs to, wherein a record is given more or less weight based on a database of origin of the record.

13. The method of claim 1, further comprising:
in response to the one or more other records having at least a specified confidence score output, creating one or more links in the first database to the one or more other databases; and
updating one or more weighted scores via the one or more links.

14. The method of claim 1, wherein:
the first database includes data entered using a first data reliability standard;
the one or more other databases include data entered using one or more other data reliability standards different from the first data reliability standard; and
a weighted score for a particular attribute type further accounts for the reliability standard of the database containing the particular attribute type.

15. The method of claim 14, wherein the data reliability standards provide a degree of confidence for data from a specific database, and wherein databases with a higher reliability standard may be considered to have increased relevance.

16. A method of associating healthcare records in healthcare databases with an individual, the method comprising:
calculating a confidence score output for a first record in a first database and one or more other confidence score outputs for each of one or more other records in one or more other second databases, different from the first database, based on a comparison of at least one attribute type located in the first record and one or more similar attribute types located in the one or more other records, via a first weighted score for each one of the at least one attribute types in the first record and an other weighted score for each one of the one or more similar attribute type in the one or more other record, wherein a confidence score output of a record is based on all weighted scores of that record and indicates a likelihood that record is associated with the individual;
wherein the first weighted score for each one of the at least one attribute type in the first record and the other weighted score for each one of the one or more similar attribute types in the one or more other records are determined based on a comparison of the at least one attribute type in the first record and each of the one or more similar attribute types in the one or more other records, wherein a weighted score for a particular attribute type indicates a likelihood that the located particular attribute type associated with the same individual as at least one other attribute type located in another record; and
wherein a weighted score for a particular attribute type of a particular record accounts for a time delta between measurements of the particular attribute type in the particular record and measurements of one or more similar attribute types in one or more other records.

17. The method of claim 16, carried out by processor execution of software code from a computer program product embodied in a computer readable storage medium.

18. The method of claim 16, wherein:
the first weighted score is reduced for the at least one attribute type in response to detecting the at least one attribute type is an easily changed attribute type and is given less weight than a fixed attribute type in calculating the confidence score output, whereas the first weighted score is not reduced for the at least one attribute type when determined to be a fixed attribute type;

the easily changed attribute type is an attribute that may change over time or is subject to more than one interpretation; and the easily changed attribute type is given less weight than a fixed attribute type in calculating an overall confidence score output;

the method further comprising:

learning from a previous comparison that the at least one attribute type is the easily changed attribute type by determining that two records are for a selected individual and that the two records have different data for the selected attribute type.

19. The method of claim 16, further comprising:

during the calculating of a confidence score output, increasing or reducing a weight given to one or more attribute types based on an institution the one or more attribute types belongs to; and wherein a record is given more or less weight based on a database of origin of the record.

20. The method of claim 16, further comprising:

in response to the second record having at least a specified confidence score output, creating one or more links in the first database to the second database; and updating one or more weighted scores via the one or more links;

wherein the first database includes data entered using a first data reliability standard, wherein the one or more other databases include data entered using one or more other data reliability standards different from the first data reliability standard, and wherein a weighted score for a particular attribute type further accounts for the reliability standard of the database containing the particular attribute type.

* * * * *